United States Patent [19]

Crace

[11] Patent Number: 4,832,942
[45] Date of Patent: May 23, 1989

[54] TOUCH EFFECTIVE DISINFECTANT TAPE

[76] Inventor: Robert L. Crace, 1024 Willow Creek Rd., Prescott, Ariz. 86301

[21] Appl. No.: 111,362

[22] Filed: Oct. 21, 1987

[51] Int. Cl.$^4$ .............................................. B32B 3/26
[52] U.S. Cl. ........................................ 428/40; 428/71;
428/76; 428/305.5; 15/244.3
[58] Field of Search ...................... 428/40, 71, 75, 76,
428/138, 132, 305.5, 308.4, 321.1, 79, 907;
15/244.3, 244.4

[56] References Cited

U.S. PATENT DOCUMENTS

| | | | |
|---|---|---|---|
| 1,491,780 | 4/1924 | Abbott | 422/305 |
| 1,783,097 | 11/1930 | Polcari | 292/347 |
| 2,527,955 | 10/1950 | Pagel | 422/291 |
| 2,763,885 | 9/1956 | Lyons | 15/244.3 |
| 3,130,505 | 4/1964 | Markevitch | 428/907 |
| 3,314,746 | 4/1967 | Millar | 422/123 |
| 4,188,447 | 2/1980 | Ehlenz | 15/244.4 |
| 4,323,656 | 4/1982 | Strickman et al. | 15/244.4 |
| 4,575,891 | 3/1986 | Valente | 428/76 |
| 4,603,069 | 7/1986 | Hag et al. | 428/138 |

FOREIGN PATENT DOCUMENTS 2837136 3/1980 Fed. Rep. of Germany ... 428/305.5
179882 7/1962 Sweden ................................ 428/907

Primary Examiner—Nancy A. B. Swisher
Attorney, Agent, or Firm—Joseph P. Burke

[57] ABSTRACT

The present disclosure is directed to a touch-effective disinfectant tape suitable for mounting on a substrate facility to enable a user to disinfect his/her hand(s) during use of such facility. This tape can be enclosed in a liquid-proof covering, e.g., shrink sealed package, aluminum or other metal foil, etc., and has an upper perforate tape cover layer, a central liquid disinfectant-containing foam layer, a double adhesive-backed lower layer and a bottom release liner. For application to the substrate, the release liner is removed and the bottom adhesive layer is applied to the door knob, door plate, urinal handle, commode handle, or other surface. When such surface is touched by the hands of the person(s) using such facility, the user's hand(s) are disinfected/-sterilized without any conscious effort on the user's part to accomplish such.

12 Claims, 2 Drawing Sheets

U.S. Patent May 23, 1989 Sheet 1 of 2 4,832,942
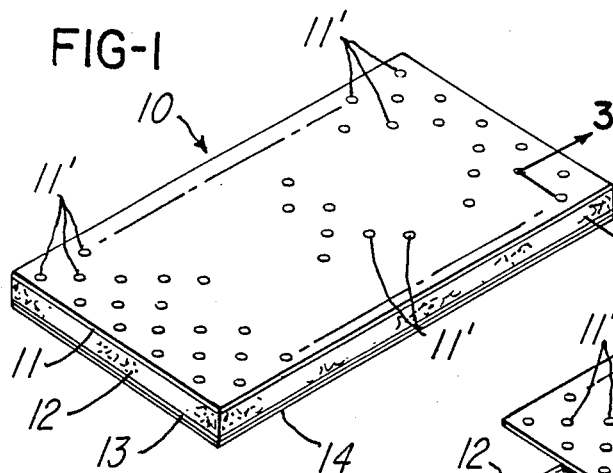
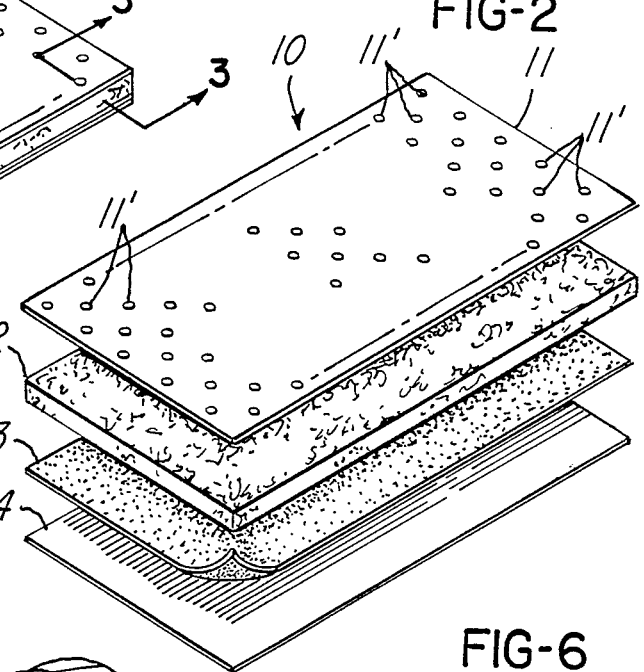
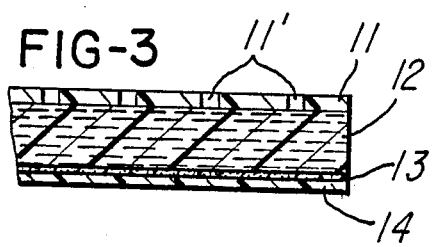
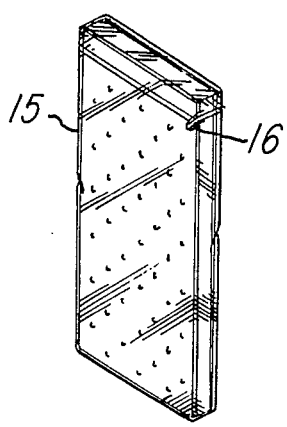
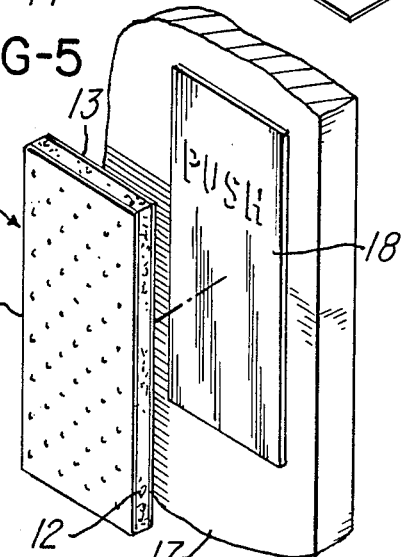
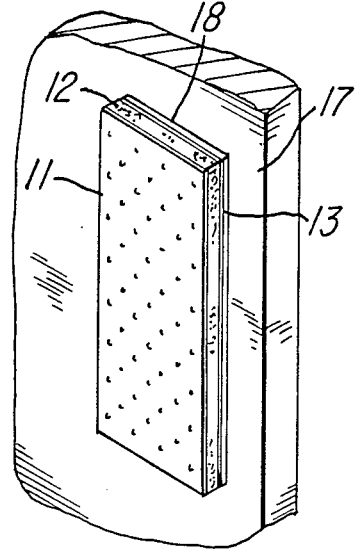
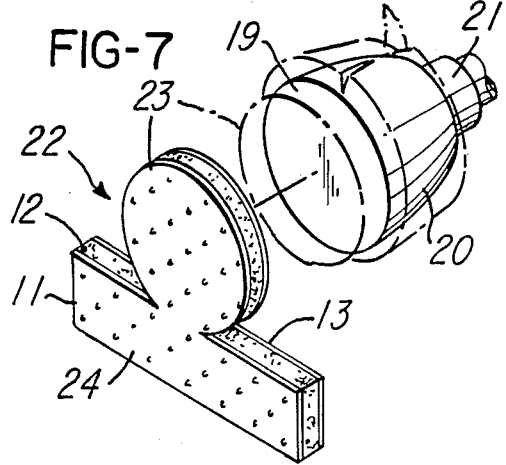
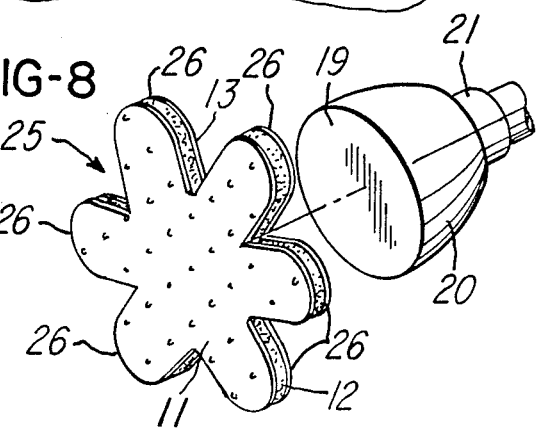

TOUCH EFFECTIVE DISINFECTANT TAPE

BRIEF DESCRIPTION OF THE INVENTION

The present invention is directed to a touch-effective disinfectant tape suitable for mounting on a substrate facility to enable a user to disinfect his/her hand(s) during use of such facility. This tape can be enclosed in a liquid-proof covering, e.g., shrink sealed package, aluminum or other metal foil, etc., and has an upper perforate tape cover layer, a central liquid disinfectant-containing foam layer, a double adhesive-backed lower layer and a bottom release liner. For application to the substrate, the release liner is removed and the bottom adhesive layer is applied to the door knob, door push plate, urinal handle, commode handle, or other surface. When such surface is touched by the hands of the person(s) using such facility, the user's hand(s) are disinfected/sterilized without any conscious effort on the user's part to accomplish such.

BACKGROUND OF THE INVENTION AND PRIOR ART

Restrooms are places where bacteria, viruses and other disease-producing substances tend to congregate. In public bathrooms, the problem is particularly accentuated because these facilities are designed to dispose of large volumes of human waste, which contains up to thirty percent bacteria. It is not unusual to find disease causing organisms on a variety of surfaces in a public bathroom, e.g., toilet seats, urinal and commode flush handles, faucet handles, door knobs and push plates, etc. Urine, feces and other body wastes which contain [bacteria, viruses, etc. can] be left on such surfaces. Various diseases carried by fecal-borne bacteria, such as salmonella and shigella, pose a threat of diahrrea and other potentially severe intestinal disorders. These germs are excreted in the feces of an infected person and, through hand transmission, can be deposited on such surfaces. If a public restroom user touches such contaminated surfaces(s) and puts his hand(s) in his mouth or touches and eats food before thoroughly washing his hands, he may contract the disease. Cold and flu viruses can also be deposited on various bathroom surfaces through hand transmission. These germs tend to thrive on door knobs and faucet handles. Unlike salmonella and shigella, which must usually be consumed to do damage, cold and flu viruses can infect persons who touch their contaminated hands to their eyes, nose or mouth. Other bacteria types found in public restrooms include those of the micrococcaceae family (which can cause boils, pimples, and other symptoms of staph infections), streptococceae (strep throat and pneumonia), pseudomonadaceae (urinary tract infections), and enterbacteria (responsible for typhoid fever as well as salmonella and shigella). The virus which causes hepatitis A is another danger.

Germs, especially fecal bacteria, can also be shot into the air when a toilet flushes. The resultant spray can land on the toilet seat, as far away as the sink and can settle on surfaces throughout the bathroom.

The present invention enables and indeed even requires, anyone touching the areas to which the disinfectant tape of this invention has been applied to disinfect (sterilize) at least that portion of their hands which is in contact with them by simply touching same.

Numerous problems in the spread of communicable disease are encountered in hospitals where sick people congregate. It is a well known fact that about 5% or more of patients entering hospitals without infection contract infection, e.g. staphlyococcus, streptococcus, etc., or diseases while in the hospital. Despite hospital regulations requiring nurses, doctors and other hospital personnel who treat or care for patients to wash and disinfect their hands after treating one patient and before treating another, this practice is often ignored. Thus the use of the disinfectant (sterilizing) tapes of this invention on hospital room door plates and door knobs results in automatic effective disinfection of the hand(s) of these medical professionals, viz., without any conscious effort on their part, as they proceed from patient to patient.

Various attempts have been made in prior art patents to sanitize door knobs. U.S. Pat. No. 3,314,746 issued to R. Y. Millar is directed to an ultra-violet light built into a door knob or door handle to irradiate the handle with ultra-violet light.

U.S. Pat. No. 1,783,097 issued to B. Polcary is directed to a hollow door knob carrying a disinfectant in its interior and having perforations distributed over its shell for the escape of minute portions of the disinfectant from the inside portion of the knob to the outside surface thereof. The disinfectant is made in the form of round balls or pills which tumble about inside the knob as it is rotated.

U.S. Pat. No. 1,491,780 issued to C. P. Abbott is directed to a hollow door knob equipped with provision for receiving and holding a quantity of crystalline substance in a more or less comminuted form, adapted to slowly and gradually give off a vapor or mist capable of disinfecting and sterilizing the handle.

U.S. Pat. No. 2,527,955 issued to R. Pagel reveals door push plates or knobs containing either a cavity within the door stile covered by a push plate filled with a fluid absorbing sponge of cellulosic material which is impregnated with a slowly evaporating disinfectant, or a hollow door knob provided with such material for the purpose of disinfecting same. The hollow door knob contains a plurality of openings in its surface to permit the escape of the disinfectant fluid or vapor.

BRIEF DESCRIPTION OF THE DRAWINGS

FIG. 1 is an overall perspective view of the touch-effective disinfectant tape of this invention.

FIG. 2 is an isometric view of the touch-effective disinfectant tape of this invention illustrating the vertical positioning arrangement with the various layers separated.

FIG. 3 is a sectional view of the disinfectant tape of this invention taken along the lines 3—3 of FIG. 1.

FIG. 4 is a standing perspective view of the disinfectant tape of this invention enclosed within an outer covering layer containing a tear strip for access.

FIG. 5 is an isometric view of the disinfectant tape of FIG. 4 after removal of the cover layer and prior to application in its environment of use on a door push plate.

FIG. 6 is a perspective view of the disinfectant tape of FIG. 5 after application to and in place on a door push plate.

FIG. 7 is an isometric view of one embodiment of a door knob disinfectant tape shown in its environment of use with a door knob.

FIG. 8 is another embodiment door knob disinfectant tape of this invention of the star shape.

DETAILED DESCRIPTION OF THE INVENTION

Figure 9:
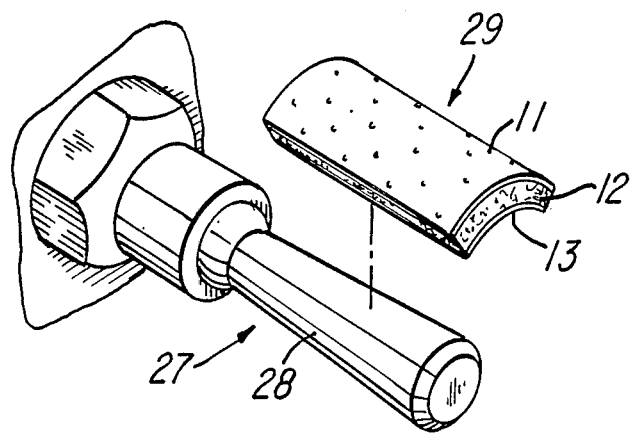
FIG. 9 is a perspective view of an arcuate-shaped disinfectant tape of this invention intended for use with a urinal handle.

As will be apparent from FIG. 1, disinfectant tape 10 is comprised of perforated cover layer 11 in contact with underlying disinfectant-impregnated foam layer 12 which in turn contacts the upper side of doubly-adhesive backed layer 13 whose lower surface is adhered temporarily to release liner layer 14. In accordance with this invention, the foam layer can be plastic, e.g., polyurethane, or natural or synthetic rubber foam. A liquid, preferably an aqueous disinfectant and/or sterilizing solution, is employed. The disinfectant/sterilizing solution utilized to impregnate the foam layer 12 can contain a wide variety of disinfectant and/or sterilizing materials, e.g. ethyl alcohol, phenyl phenol, iodine solutions, chlorine and hypochlorite solutions, etc., depending upon the particular bacteria, virus, etc., desired to be combatted. Moreover a mixture of two or more disinfectant/sterilizing materials can be employed in the impregnated disinfectant solution.

The perforated tape cover layer 11 can be made of any material, e.g., plastic or plastic-coated paper which is resistant to penetration or migration of such liquid disinfectant/sterilizing material except at the locations of the openings 11'. Suitable materials for use as the perforated cover layer 11 include, but are not necessarily limited to, the following: polyethylene, polypropylene, polyethylene-coated paper, polypropylene-coated paper, etc. Suitably perforate tape upper layer 11 contains from about 40% to about 80% open area due to openings 11'. In accordance with a preferred embodiment of this invention, perforated tape cover layer 11 is flexible.

Beneath the disinfectant/sterilizing-impregnated foam layer 12 is a double adhesive-backed layer 13 which serves to temporarily adhere layer 12 to the release liner 14 until the latter is removed therefrom prior to application of the disinfectant tape to the substrate to which it is to be applied, e.g., door plate, door knob, etc. Doubly adhesive-backed layer 13 can be made of paper, plastic, plastic coated paper, etc. Any suitable functionally adhesive material can be used on both upper and lower surfaces of layer 13 provided that it is capable of adhering to both foam layer 12 and the metal or other material from which the door plate, door knob, commode handle, etc., is made.

The touch-effective disinfectant tape 10 is then enclosed (FIG. 4) in a suitable outer covering material 15, e.g., a heat shrinkable plastic, such as polyvinyl chloride, or a metal foil material, such as aluminum foil, in order to preserve the disinfectant liquid material with which the foam layer 12 is impregnated and prevent it from evaporation along with the aqueous carrier or solvent in which it is dissolved/dispersed.

Both tape cover layer 11 and outer covering layer 15 can be colored, can have printing or other indicia on one, more or all outer surface(s) thereof and can assist in the marketability of the disinfectant tapes.

As is shown in FIG. 4, heat shrinkable plastic layer 15 provides a covering and encapsulates disinfectant tape 10. The covering material can be provided with a tear strip 16 to enable the user to gain access to the tape prior to applying it. As is shown in FIG. 5, upon removal of the covering layer 15, the disinfectant tape 10 can be ready for application to the substrate on which it is to be mounted, simply by removal of the release liner 14. Disinfectant tape 10 is shown in FIG. 5 with the release liner 14 removed and in FIG. 6 as applied to the push plate 18 of door 17.

The disinfectant tape of this invention can be made in several ways. According to one method, layers 14, 13 and 12 are laid up in the form of long sheets in the vertical relationship shown in FIG. 2. The upper surface of foam layer 12 is then impregnated with the disinfectant/sterilizing solution and perforated tape cover layer 11 is then applied to the upper side of impregnated foam layer 12. The desired tape shapes can then be stamped from such sheets. Heat sealing dies can be used for stamping resulting in marginally sealing perforated outer tape layer 11 to impregnated foam layer 12 around the periphery of the stamped shaped individual tapes. Outer covering 15 is then applied.

Alternatively, layers 11, 12, 13 and 14 can be laid up in the positional arrangement shown in FIG. 2. Then holes 11' are punched through outer tape layer 11 causing portions of the punched out plastic to penetrate into the upper portion of foam layer 12. The disinfectant liquid can then be impregnated downwardly through openings 11' prior to applying the outer covering layer 15.

Another procedure for forming disinfectant tape 10 is to punch openings 11' in tape cover layer 11. Then adhesive can be applied to the bottom surface of layer 11 at locations between openings 11' and the thus adhesively coated surface laid up on the upper surface of foam layer 12. Once the adhesive has dried, the disinfectant liquid can then be impregnated downwardly through openings 11' and outer covering layer 15 can then be applied.

FIG. 7 illustrates one embodiment of a door knob disinfectant tape 22 which is composed of integral pad round head portion 23 and lower rectangular (bar)-shaped base portion 24. Likewise on removal of its respective release liner, this disinfectant/sterilizing tape can be applied to the door knob by pressing the adhesive-backed surface 13 of pad head portion 23 to the door handle face portion 19 and wrapping the pad base portion 24 around the door handle gripping portion 20. Upon rotation of the door handle by a person seeking access through the door and turning same to rotate the door handle stem 21, the fingers and palm hand portions of the person turning the door knob are automatically disinfected, viz., without any conscious effort being required on his/her part to do so.

Similarly, integral star-shaped configuration door knob tape 25, having a plurality of radial finger portions 26, can be applied to the face and gripping sections of the door knob illustrated in FIG. 8 with the central portion of the star being applied to the face portion 19 of the door knob and the radial finger portions 26 being folded thereupon the door handle gripping section 20 so that after folding, said fingers face toward door handle stem 21. Similarly, upon touching of the perforated cover layer 11 of star-shaped door knob tape 25, the touching hand portions of the person turning the door knob will be automatically disinfected/sterilized.

FIG. 9 illustrates the application of urinal flush handle tape 29, which is shown to be of arcuate shape, to the gripping section 28 of urinal flush handle 27. The arcuate shape of the tape conforms generally to the outer curvature of the urinal flush handle.

Figure 10:
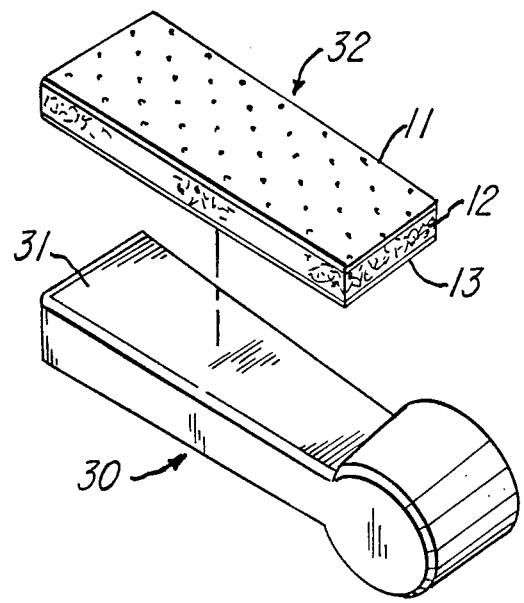
FIG. 10 is an isometric view of a disinfectant tape of this invention suitable for use in its environment on a commode handle.

FIG. 10 illustrates the application of commode flush handle disinfectant tape 32 to the upper one of the gripping sections or areas 31 of commode flush handle 30 to accomplish the disinfection/sterilization desired.

Thus it will be appreciated that there have been illustrated and described various forms of automatically touch-effective disinfectant tapes suitable for mounting on substrate facilities to enable the user to automatically disinfect/sterilize his/her hand(s) while using such facility. This tape can be, and preferably is, enclosed in a liquid-proof outer covering and is comprised of an upper perforate tape cover layer, a central liquid disinfectant/sterilizing-impregnated foam layer, a double adhesive-backed lower layer and a bottom release liner layer. Upon removal of the release liner, the bottom of the double adhesive-backed lower layer can be directly applied to the door knob, door plate, urinal handle, commode handle, or other facility's surface to enable the hands of the person(s) touching same to be disinfected/sterilized without requiring any conscious effort on their part.

Upon evaporation or other loss of liquid disinfectant, the tape of this invention can be removed from the substrate and any accumulated adhesive cleaned therefrom. A fresh disinfectant tape can then be applied and the previous one can be disposed of, thereby enhancing the hygiene and disinfectant efficiency of the bathroom, etc. in which such tapes are used.

What is claimed is:

1. A touch-effective disinfectant tape comprising a perforate tape upper layer, a central liquid disinfectant-containing foam layer, a double adhesive backed lower layer and a bottom release liner, wherein the users hand(s) are disinfected/sterilized upon touching said upper layer without requiring any conscious effort on the user's part.

2. A touch-effective disinfectant tape as in claim 1 enclosed within an outer covering layer.

3. A touch-effective disinfectant tape as in claim 2 wherein said outer covering layer includes a tear strip.

4. A touch-effective disinfectant tape as in claim 2 wherein said outer covering layer is heat-shrinkable plastic.

5. A touch-effective disinfectant tape as in claim 2 wherein said outer covering layer is metal foil.

6. A touch-effective disinfectant tape as in claim 5 wherein said metal foil is aluminum foil.

7. A touch-effective disinfectant tape as in claim 1 wherein said perforate upper layer is plastic.

8. A touch-effective disinfectant tape as in claim 7 wherein said plastic is flexible.

9. A touch-effective disinfectant door knob tape as in claim 1 having an integral round head portion for application to the door knob face and a rectangular base portion for application to the door knob gripping portion.

10. A touch-effective disinfectant door knob tape as in claim 1 having an integral star-shaped configuration having a central portion for application to the door knob face and a plurality of radial finger portions for application to the door knob gripping portion.

11. A touch-effective disinfectant urinal flush handle tape as in claim 1 having an arcuate shape conforming generally to the outer curvature of said urinal flush handle.

12. A touch-effective disinfectant tape as in claim 1 wherein said perforate tape upper layer contains from about 40 percent to about 80 percent open area.

* * * * *